United States Patent
Wood et al.

(10) Patent No.: US 6,868,221 B1
(45) Date of Patent: Mar. 15, 2005

(54) FIBER OPTIC POSITIONER

(75) Inventors: Leroy M. Wood, Buffalo, NY (US); William R. Potter, Grand Island, NY (US); Kenneth R. Weishaupt, Hamburg, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 10/434,420

(22) Filed: May 8, 2003

Related U.S. Application Data

(60) Provisional application No. 60/378,818, filed on May 8, 2002.

(51) Int. Cl.[7] ................................................ G02B 6/46
(52) U.S. Cl. ............................ 385/137; 604/20; 606/15
(58) Field of Search ................................. 385/117, 118, 385/136, 137; 604/20; 606/15, 16, 17

(56) References Cited

U.S. PATENT DOCUMENTS 5,671,317 A * 9/1997 Weishaupt et al. .......... 385/137

* cited by examiner

*Primary Examiner*—Khiem Nguyen
(74) *Attorney, Agent, or Firm*—Rogalsky & Weyand, LLP

(57) ABSTRACT

The present invention relates to an apparatus which includes a polypod support which includes a fiber optic supporting platform. The fiber optic supporting platform includes an opening. The apparatus further includes at least three legs forming a tripod, each of the legs having two ends, a first end being secured to the fiber optic supporting platform and the second end being adapted for attachment to the skin of the patient, a first tube having an outer diameter, a second tube having an outer diameter and an inner diameter, where the inner diameter of the second tube surrounds the outer diameter of the first tube and where the outer diameter of the second tube is slidably mounted within the opening of the fiber optic surrounding platform and a fiber optic.

12 Claims, 3 Drawing Sheets

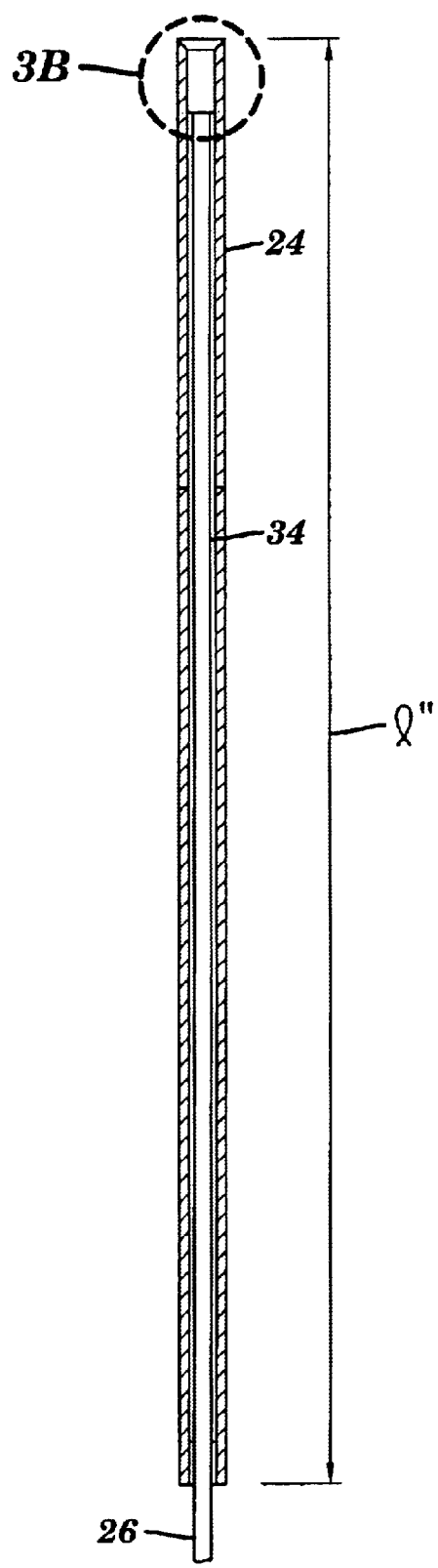
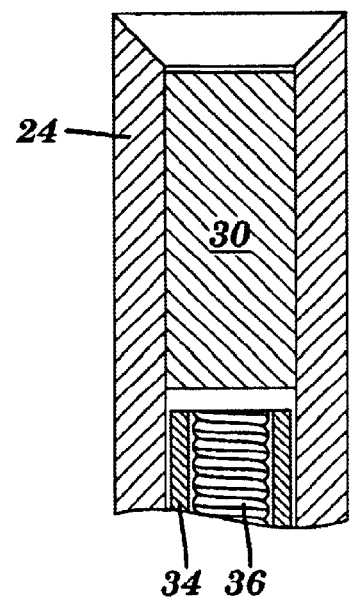
FIG. 3A
FIG. 3B

FIBER OPTIC POSITIONER

This application claims priority to Provisional Patent Application Ser. No. 60/378,818, filed May 8, 2002, which is hereby incorporated by reference.

This invention was made with funding from the National Institute of Health grant number CA55791. The United States Government may have certain rights in the invention.

BACKGROUND OF THE INVENTION

This invention relates to fiber optics and more particularly relates to the use of fiber optics for medicinal purposes where the fiber optic is used to deliver radiation to or receive radiation from a patient.

Fiber optics are of increasing importance in both medical imaging and treatment. For example, in the area of photodynamic therapy, where a patient is injected with a photodynamic therapeutic agent followed by irradiation, fiber optics have become a radiation delivery method of choice. As with all new technologies, there have, however, been problems associated with the used of fiber optics as a delivery mechanism.

In particular when a fiber optic, or, for that matter, other light sources, are used to deliver light energy to the skin of a patient for the purpose of irradiating a particular defined area, e.g. a skin tumor, there has been a problem with movement of the patient resulting in inaccurate delivery which can result in irradiation and irritation or necrosis of nearby healthy tissue.

In the past, attempts have been made to immobilize the patient which is not only very uncomfortable due to long times involved in light therapy, but still does not provide the accuracy needed because total elimination of patient movement is impractical if not impossible.

BRIEF DESCRIPTION OF THE DRAWINGS

The invention may be more fully understood by reference to the drawings which illustrate embodiments of the invention. It is to be understood that the embodiments are for purposes of illustrating and not limiting the present invention.

FIG. 3 shows a cross sectional view of an alternate embodiment of the present invention.

DETAILED DESCRIPTION OF THE INVENTION

The present invention relates to an apparatus which includes a polypod support which includes a fiber optic supporting platform. The fiber optic supporting platform includes an opening. The apparatus further includes at least three legs forming a tripod, each of the legs having two ends, a first end being secured to the fiber optic supporting platform and the second end being adapted for attachment to the skin of the patient, a first tube having an outer diameter, a second tube having an outer diameter and an inner diameter, where the inner diameter of the second tube surrounds the outer diameter of the first tube and where the outer diameter of the second tube is slidably mounted within the opening of the fiber optic surrounding platform and a fiber optic.

In accordance with the invention, the apparatus is used for stabilizing a fiber optic relative to the skin surface of a patient so that radiation from the fiber optic strikes a defined surface area on the skin independently of patient movement.

""Fiber optic"" as used herein means not only the fiber optic itself but also includes lenses functioning with the fiber optic, optional sheathing material around the fiber optic and other apparatus necessary or desirable to make the fiber optic function as a light source having a defined impact area upon a skin surface.

""End of the fiber optic"" means the area of the fiber optic near the light emitting or receiving portion of the fiber optic which may include supporting material, sheaths and lenses.

""Skin"" means any surface area of a patient having a surrounding area large enough to support a polypod of the invention.

""Polypod"" means a multileg apparatus. Such a polypod may have from as few as three to an infinite number of legs, e.g. in the form of a supporting cone. The polypod of the invention is usually a tripod or a conical section. In accordance with the invention, the ends of the legs attached to the skin are more distally separated than the ends of the legs attached to the platform and are arranged so that force upon the platform from any direction is resisted by at least one of the legs.

""Vertical"", as used herein, means essentially perpendicular to the surface of skin to which a polypod is secured.

""Essentially perpendicular"" means an angle of between 60 and 90 degrees to the surface of skin to which a polypod is secured.

In accordance with the invention, the legs may be attached to the skin in any suitable way. The preferred method of attachment is to tape feet upon the surface of the skin or glue them to the skin using a suitable adhesive such as ethylcyanoacrylate. The distal ends of the legs are attached mechanically or by adhesive to the feet. Optionally, but not preferably, the legs may be glued directly to the skin or inserted into the skin and supporting muscle.

Figure 1:
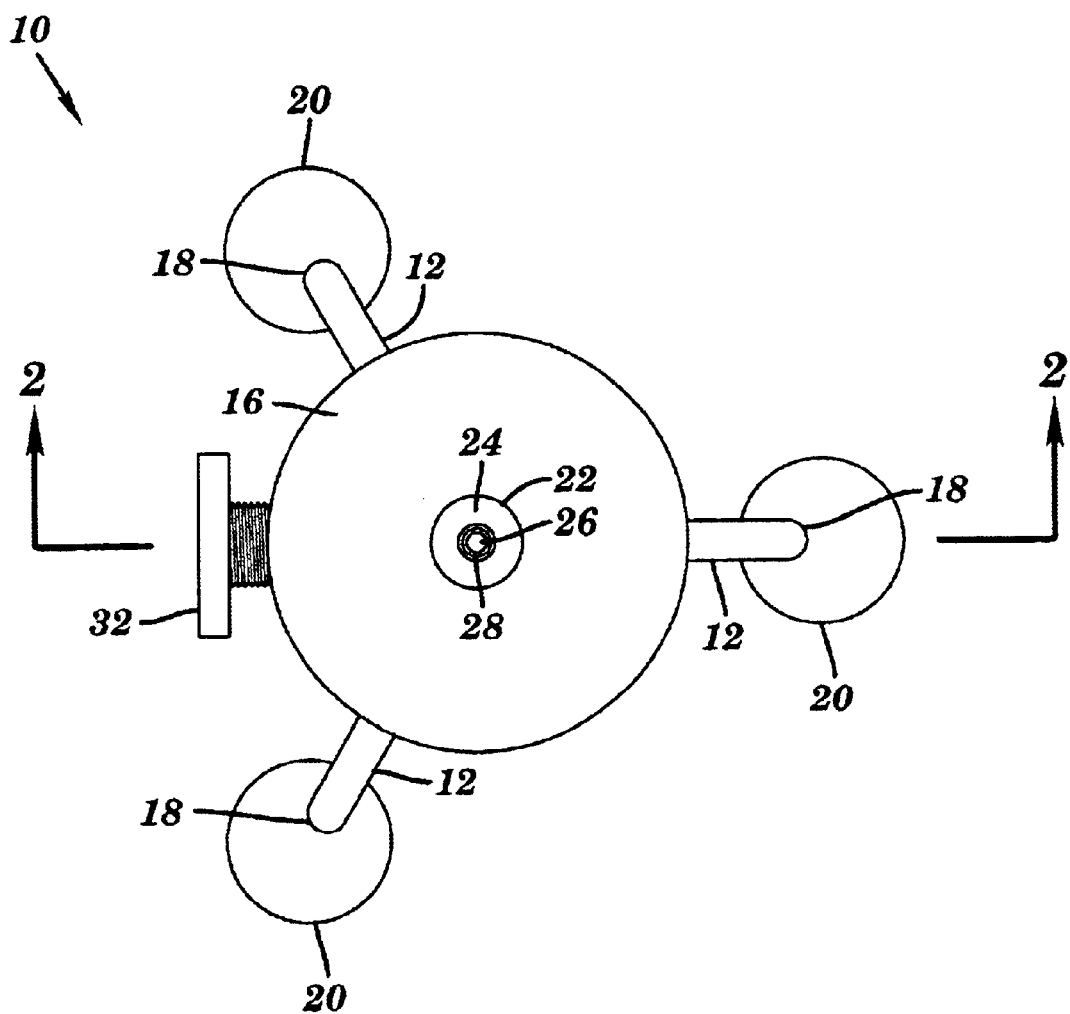
FIG. 1 shows a top view of one embodiment of the present invention.
Figure 2:
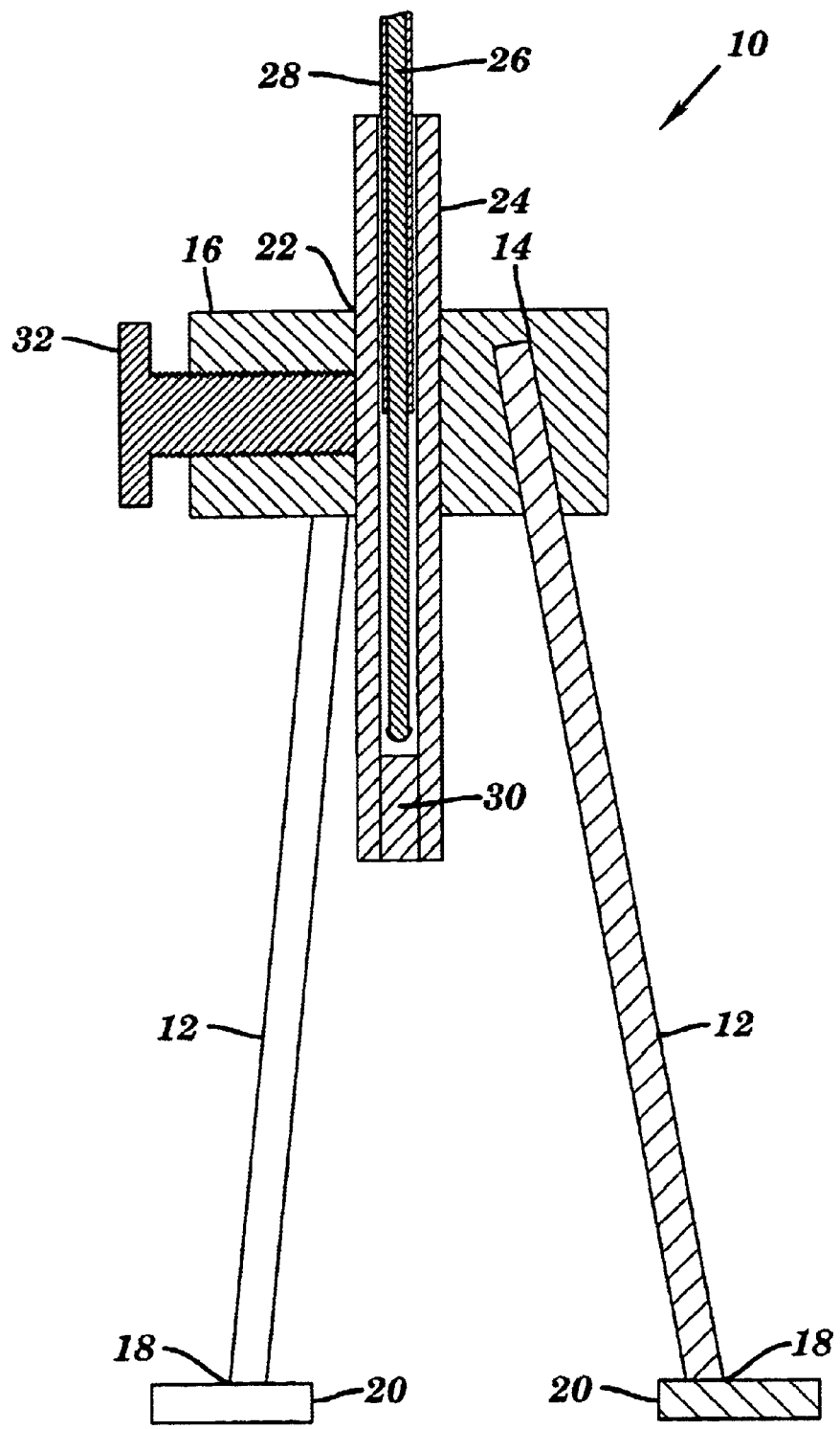
FIG. 2 shows a cross sectional elevational view the embodiment of the invention shown in FIG. 1.

As seen in FIGS. 1 and 2, in one embodiment, tripod 10 is provided with legs 12, each of which is attached at a first end 14 to fiber optic platform 16 and at their second ends 18 to feet 20. Fiber optic platform 16 is provided with an opening, such as through hole, 22 sized to accommodate a tube 24 which contains fiber optic 26. As shown in FIGS. 1 and 2, fiber optic 26 is covered by optional sheath 28. In an alternative embodiment of the present invention, fiber optic 26 includes a non-jacketed fiber, such as a 600$\mu$ quartz fiber. A non-jacketed fiber creates less weight load for tripod 10. In the shown embodiment, fiber optic 26 includes a focusing lens 30. Platform 16 is provided with a means for securing tube 24 in an essentially vertical position (within 10 degrees of vertical) in the form of thumb screw 32.

In one embodiment, tube 24 is a plastic tube, (such as styrene, polyvinyl chloride, polycarbonate and the like), having an outer diameter of from about 0.0625 to about 0.25 inches. Tube 24 is from about 2 to about 8 inches in length. In one embodiment, tube 24 is a styrene tube having an outer diameter of about 0.125 inches and a length of about 4 inches. Tube 24 is configured such that the outer diameter of tube 24 slides in through hole 22. By sliding tube 24 through hole 22, the light field of fiber optic 26 is adjusted to the required diameter.

In an alternate embodiment, as shown in FIG. 3, the inner diameter of tube 24 surrounds an outer diameter of a second tube 34. Second tube 34 is a lightweight material, such as stainless steel or plastic, having an inner diameter configured to receive a fiber optic and an outer diameter of from about 0.03 to about 0.22 inches and is from about 2 to about 8 inches in length. In one embodiment, second tube 34 is a stainless steel tube with an outer diameter configured to slide within the inner diameter of tube 24 and a length of about 3.75 inches. In one embodiment, second tube 34 is a 16 gauge hypodermic stainless steel tube. In the alternate embodiment, the inner diameter of second tube 34 surrounds the outer diameter of fiber optic 26. As further shown in an alternate embodiment in FIG. 3, buffer 36 surrounds the outer diameter of fiber optic 26 and is compacted onto fiber optic 26 with a fastener, such as a nut, to eliminate relative motion between second tube 34 and buffer 36. Buffer 36 is any suitable buffer material, such as TEFZEL®, nylon or polyethylene.

In operation, the feet 20 of tripod 10 are glued to the surface of skin surrounding a skin area to be treated. Feet 20 are attached to the skin of a patient usually by means of ethyl cyanoacrylate adhesive. Feet 20 are arranged so that they are essentially equidistant from each other (i.e. arranged at about 120°+/−10° intervals around platform 16). Furthermore, for stability, the legs extend from the platform toward the skin at an angle of from 10 to 45 degrees from the vertical.

The area of skin to be irradiated is located between feet 20 directly below lens 30. Light passes through fiber optic 26 from a source (not shown) through lens 30 to the desired skin area. Movement by the patient is thus rendered essentially irrelevant because the tripod is attached to and moves with the patient thus the relationship between the lens and the desired skin area does not vary.

While the polypod of the invention has been primarily developed for irradiation with light energy in photodynamic therapy, it is to be understood that the invention may also be used for fiber optic or scan imaging or may be used for high energy radiation applications. In such a case electronic scanning apparatus and high energy irradiation sources held by the platform may be considered equivalent to a fiber optic held by the platform, as described herein.

Although certain preferred embodiments have been depicted and described in detail herein, it will be apparent to those skilled in the relevant art that various modifications, additions, substitutions and the like can be made without departing from the spirit of the invention, and these are therefor considered to be within the scope of the invention as defined by the following claims.

What is claimed:

1. An apparatus comprising:
   a polypod support comprising a fiber optic supporting platform, wherein the fiber optic supporting platform comprises an opening;
   at least three legs forming a tripod, each of the legs having two ends, a first end being secured to the fiber optic supporting platform and the second end being adapted for attachment to the skin of the patient;
   a first tube having an outer diameter;
   a second tube having an outer diameter and an inner diameter, wherein the inner diameter of the second tube surrounds the outer diameter of the first tube and wherein the outer diameter of the second tube is slidably mounted within the opening of the fiber optic surrounding platform; and
   a fiber optic.

2. The apparatus according to claim 1 wherein the first tube is metal.

3. The apparatus according to claim 2 wherein the metal is stainless steel.

4. The apparatus according to claim 3 wherein the stainless steel is 16 gauge stainless steel.

5. The apparatus according to claim 2 wherein the second tube is plastic.

6. The apparatus according to claim 5 wherein the plastic is styrene.

7. The apparatus according to claim 5 wherein the fiber optic comprises a non-jacketed fiber.

8. The apparatus according to claim 6 wherein the fiber is surrounded by a buffer.

9. The apparatus according to claim 8 wherein the buffer is attached to the fiber with a nut.

10. The apparatus according to claim 1, wherein the polypod is a tripod.

11. The apparatus according to claim 10 wherein the second ends of the legs are provided with feet for attachment to the skin.

12. The apparatus according to claim 11 wherein the fiber optic comprises a focusing lens.

* * * * *